US010961275B2

(12) United States Patent
Bralkowski et al.

(10) Patent No.: US 10,961,275 B2
(45) Date of Patent: Mar. 30, 2021

(54) POULTRY FARM PRACTICES

(71) Applicant: Global Bioprotect IP Pty Ltd, Willoughby (AU)

(72) Inventors: Michael Paul Bralkowski, Lexington, NC (US); Sarah Ashley Brooks, Winston-Salem, NC (US); Stephen M. Hinton, Mount Pleasant, SC (US); David Matthew Wright, Kernersville, NC (US); Shih-Hsin Yang, Queensland (AU)

(73) Assignee: Global Bioprotect IP Pty Ltd, Willoughby (AU)

( * ) Notice: Subject to any disclaimer, the term of this patent is extended or adjusted under 35 U.S.C. 154(b) by 368 days.

(21) Appl. No.: 15/894,756

(22) Filed: Feb. 12, 2018

(65) Prior Publication Data

US 2018/0170968 A1 Jun. 21, 2018

Related U.S. Application Data

(63) Continuation of application No. 14/374,881, filed as application No. PCT/AU2013/000060 on Jan. 25, 2013, now abandoned.

(30) Foreign Application Priority Data

Jan. 27, 2012 (AU) .............................. 2012900312

(51) Int. Cl.
| | |
|---|---|
| *A01N 63/22* | (2020.01) |
| *C07K 14/32* | (2006.01) |
| *C07K 7/64* | (2006.01) |
| *A01N 63/00* | (2020.01) |
| *C12P 21/02* | (2006.01) |
| *C05F 5/00* | (2006.01) |
| *A01N 63/10* | (2020.01) |
| *C12R 1/12* | (2006.01) |
| *A01N 37/18* | (2006.01) |
| *C05F 11/08* | (2006.01) |
| *C09K 8/584* | (2006.01) |
| *C12R 1/125* | (2006.01) |

(52) U.S. Cl.
CPC .............. *C07K 7/64* (2013.01); *A01N 37/18* (2013.01); *A01N 63/00* (2013.01); *A01N 63/10* (2020.01); *A01N 63/22* (2020.01); *C05F 5/006* (2013.01); *C05F 11/08* (2013.01); *C07K 14/32* (2013.01); *C09K 8/584* (2013.01); *C12P 21/02* (2013.01); *C12R 1/12* (2013.01); *C12R 1/125* (2013.01); *Y02A 40/20* (2018.01)

(58) Field of Classification Search
CPC .......... C07K 14/32; C12R 1/125; A01N 63/22
See application file for complete search history.

(56) References Cited

U.S. PATENT DOCUMENTS

| | | | |
|---|---|---|---|
| 3,030,789 | A | 4/1962 | Rothernerger |
| 3,687,926 | A | 8/1972 | Arima et al. |
| 4,905,761 | A | 3/1990 | Bryant |
| 4,919,936 | A | 4/1990 | Iwanami et al. |
| 5,244,660 | A | 9/1993 | O'Brien et al. |
| 5,945,333 | A | 8/1999 | Rehberger |
| 7,011,969 | B2 | 3/2006 | Yoneda et al. |
| 7,247,299 | B2 | 7/2007 | Lin et al. |
| 7,754,469 | B2 | 7/2010 | Baltzley et al. |
| 8,025,874 | B2 | 9/2011 | Bellot et al. |
| 2012/0003199 | A1* | 1/2012 | Scherer .................. A01N 25/00 424/93.462 |

FOREIGN PATENT DOCUMENTS

| | | |
|---|---|---|
| CN | 10-1665773 A | 10/2010 |
| GB | 2 108 389 A | 5/1983 |
| JP | 6-121668 A | 3/1994 |
| WO | WO 2005/117929 A1 | 12/2005 |
| WO | WO 2009/158617 A1 | 12/2009 |
| WO | WO 2010/067245 A1 | 6/2010 |

OTHER PUBLICATIONS

Chen ("Batch Production of biosurfactant with foam fractionation" Journal of Chemical Technology and Biotechnology, 81 (2006), 1923-1931), (Year: 2006).*
EPA ("Biopesticide Regristration Action Document: Bacillus subtilis Strain QST 713 (PC Code 006479)" United States Environmental Protection Agency, Office of Pesticide Programs, Biopesticides and Pollution Prevention Division, Washington DC, file name dated Aug. 9, 2006, webcapture attached (Year: 2006).*
Errington ("Regulation of Endospore Formation in Bacillus Subtilis", Nature Reviews, vol. 1, 2003, 117-126) (Year: 2003).*
Serenade ASO ("Serenade ASO", Agraquest, California, Organic Materials Review Institute, 2007). (Year: 2007).*
Bento, "Diversity of biosurfactant producing microorganisms isolated from soils contaminated with diesel oil," Microbiological Research, 160:249-255 (2005).

(Continued)

*Primary Examiner* — Robert J Yamasaki
*Assistant Examiner* — Charles Zoltan Constantine
(74) *Attorney, Agent, or Firm* — Perkins Coie LLP

(57) ABSTRACT

The present invention relates to methods of improving the environment within a poultry farming facility including reducing ammonia production in a poultry facility, inhibiting urease enzymes in poultry litter, reducing levels of pathogenic bacteria in poultry litter, improving productivity of poultry farms, reducing or preventing pododermatitis in poultry reared in mass production poultry facilities and controlling pests in poultry litter. Compositions, suitable for use in such methods, comprising at least one microorganism of the genus *Bacillus* and at least one biosurfactant wherein the biosurfactant is present in an amount of 2 mg/L to 7000 mg/L are also described.

10 Claims, 1 Drawing Sheet

(56) References Cited

OTHER PUBLICATIONS

Cooper et al., "Enhanced Production of Surfactin from Bacillus subtilis by Continuous Product Removal and Metal Cation Additions," Applied and Environmental Microbiology, 42:408-412, (1981).

Coutte et al., "Production of surfactin and lengycin by Bacillus subtilis in a bubbleless membrane bioreactor," Applied Microbiology and Biotechnology, 87:499-507 (2010).

International Search Report, International Application No. PCT/AU2013/000060 (published under WO 2013/110133), 5 pages (dated Mar. 1, 2013).

Kim et al., "Production and Properties of a Lipopeptide Biosurfactant from Bacillus subtilis C9," Journal of Fermentation and Bioengineering, 84(1):41-46 (1997).

Mulligan et al., "Enhanced biosurfactant production by a mutant Bacillus subtilis strain," Applied Microbiology and Biotechnology, 31:486-489 (1989).

Piggot, "Sporulation of Bacillus subtilis," Current Opinion in Microbiology, 7:579-586 (2004).

Shaligram, "Surfactin—A review of Biosynthesis, Fermentation, Purification and Application," Food Technology and Biotechnology, 48(2):119-134 (2010).

Sheppard et al., "The production of surfactin by Bacillus subtilis grown on peat hydrolysate," Applied Microbiology and Biotechnology, 27:110-116 (1987).

Siebring, "Repeated triggering of sporulation in Bacillus subtilis selects against a protein that affects the timing of cell division," The International Society for Microbial Ecology, 8:77-87 (2014).

Sultan et al., "Effect of Probiotic on some Physiological Parameters in Broiler Breeders," International Journal of Poultry Science, 10(8):626-628 (2011).

Tam, "The intestinal Live Cycle of Bacillus subtillis and Close relatives," Journal of Bacteriology, 188(7):2692-2700 (Apr. 2006).

US Department of Agriculture, Agricultural Research Service, ARS Culture Collection NRRL, available at: http://nrrl.ncaur.usda.gov/cgi-bin/usda/prokaryote/report.html?nrrlcodes=B%2d3383, 1 page (downloaded on Feb. 20, 2015).

Wei et al., "Enhancement of surfactin production in iron-enriched media by Bacillus subtilis ATCC 21332," Enzyme and Microbial Technology, 22:724-728 (1998).

Wei et al., "Optimizing Iron Supplement Strategies for Enhanced Surfactin Production with Bacillus subtilis," Biotechnology Program, 20:979-983 (2004).

Wright, "Rapid and Improved Assay of Surfactins from Bacillus subtilis, 203R via UPLC-ESI-MS," Master Thesis submitted to the Faculty of the Graduate School at The University of North Carolina at Greensboro, 43 pages (2018).

Yeh, "Enhanced Production of Surfactin from Bacillus subtilis by addition of Solid Carriers," Biotechnology Progress, 21(4):1329-1334 (2005).

* cited by examiner

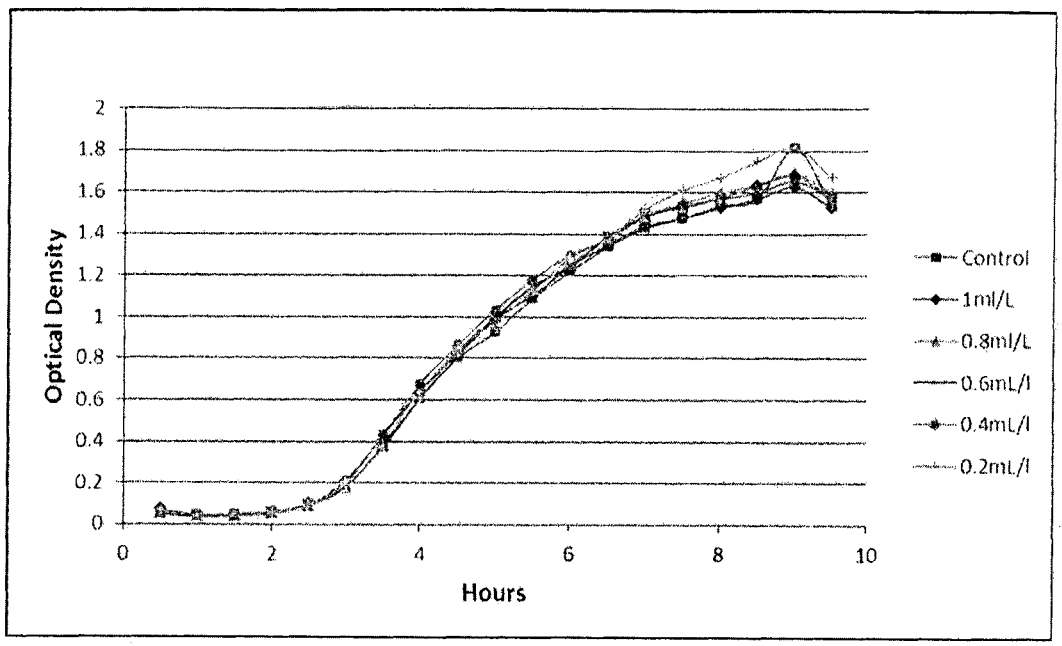

POULTRY FARM PRACTICES

CROSS-REFERENCE TO RELATED APPLICATIONS

This application is a continuation of U.S. patent application Ser. No. 14/374,881, which is a 371 filing of International Application No. PCT/AU2013/000060 filed Jan. 25, 2013, entitled "IMPROVED POULTRY FARM PRACTICES," which claims the benefit of Australian Patent Application No. 2012900312 filed Jan. 27, 2012, entitled "METHOD OF PRODUCING BIOSURFACTANTS," the contents of each of which applications is hereby incorporated by reference in its entirety.

FIELD OF THE INVENTION

The present invention relates to methods of improving the environment within a poultry farming facility including reducing ammonia production in a poultry facility, inhibiting urease enzymes in poultry litter, reducing levels of pathogenic bacteria in poultry litter, improving productivity of poultry farms, reducing or preventing pododermatitis in poultry reared in mass production poultry facilities and controlling pests in poultry litter. Compositions, suitable for use in such methods, comprising at least one microorganism of the genus *Bacillus* and at least one biosurfactant wherein the biosurfactant is present in an amount of 2 mg/L to 7000 mg/L are also described.

BACKGROUND OF THE INVENTION

To provide food for an increasing population, the total production of grains, meats, vegetables and dairy products has increased 70% in the past 50 years. Correspondingly, the growth of the poultry industry has dramatically increased. The US value of production of broilers, eggs, turkeys and chickens in 2010 was USD $34.7 billion, increased by 10% from 2009. US poultry exports approached 7 billion pounds in weight for each year 2008 to 2010. Furthermore, there is increased interest in the speciality chicken foot section of the poultry market.

To sustain poultry production and growth in poultry production, mass production facilities that house tens of thousands to millions of birds are common in poultry farming. However, these facilities have production problems that are deleterious to bird health and result in slower feeding, low weight and/or cause disease in the bird population.

The close proximity of the poultry in the mass facilities means that the birds are in contact with not only their own faeces but also the faeces of other birds. This results in gastrointestinal pathogens spreading quickly through a facility. Some gastrointestinal pathogens of poultry, such as *Salmonella* spp., *Clostridium* spp., *Camplylobacter* spp., and *Escherichia* spp., are also pathogenic to humans and their levels in poultry farms are monitored.

Levels of pathogenic bacteria in poultry populations have traditionally been controlled by administration of antibiotics to the poultry. However, in recent years some countries, such as European countries, have banned the use of antibiotics that are also used in humans, because of the emergence of antibiotic resistant pathogenic bacteria.

One means of overriding pathogenic bacteria in poultry has been to add probiotic microorganisms to their feed and this has been found to improve bird health, meat production and egg production (Khalid et al., "Effect of Probiotic on some Physiological Parameters in Broiler Breeders", International Journal of Poultry Science, 2011, 10(8): 626-628).

The probiotics fed to poultry may include non-pathogenic microorganisms such as *Bacillus subtilis* (U.S. Pat. Nos. 4,919,936, 7,247,299 and 7,754,469). However, these compositions must be suitable for consumption by the poultry and any additional feed additives with antibiotic activity may be regulated by industry regulators.

Furthermore, some of the pathogenic bacteria include urease enzymes that hydrolyze urea and uric acid found in poultry faeces and thereby produce ammonia. High levels of ammonia in the facilities is deleterious to bird health and industry regulations require ammonia levels in mass production poultry facilities to be kept below 25 ppm.

Control of ammonia levels is currently achieved over the first 8 to 10 days of production by use of an acidic neutralizing chemical added to the litter. Common acidic neutralizing chemicals include sulfate salts, bisulfite salts and organic acids such as citric acid. However, these neutralizing chemicals are only active during initial production and are consumed by about day 10 of production. Subsequently ammonia control is achieved using ventilation fans. Another difficulty with the use of acidic neutralizing chemicals is that they are in constant contact with the feet of the birds and cause or exacerbate pododermatitis caused by *Staphylococcus* infection and blistering of their feet.

Compositions comprising *Bacillus* spp., have also been used in deodorising compositions due to their ability to excrete extracellular enzymes that breakdown waste (U.S. Pat. No. 8,025,874). One of these compositions comprises a specific strain of *Bacillus subtilis*, NRRL B-50147, and is particularly useful for controlling odour in animal bedding. However these compositions require the use of specific strains of *B. subtilis* and also include other adsorbents such as clay. Such compositions are also not indicated as suitable for large scale use in environments such as mass production poultry farms.

There is a need for an effective treatment of mass production poultry facilities to reduce and/or control ammonia production and that is effective in controlling and/or reducing pathogenic bacteria in poultry litter and poultry manure thereby reducing odour, preventing infection in the poultry and consumers and improving poultry health and productivity.

SUMMARY OF THE INVENTION

The present invention is predicated in part on the discovery that a composition comprising at least one *Bacillus* microorganism and at least one biosurfactant, such as surfactin, is useful in controlling pathogenic bacteria and the production of ammonia in mass production poultry farming facilities.

In one aspect of the invention, there is provided a method of improving the environment within a poultry farming facility comprising applying to poultry litter or poultry manure within the poultry farming facility a composition comprising at least one microorganism of the genus *Bacillus* and at least one biosurfactant, wherein the biosurfactant is present in the composition in an amount of between about 2 mg/L and 7000 mg/L.

In some embodiments, the environment is improved by controlling or reducing the production of ammonia in the poultry farming facility. In some embodiments, the control or reduction in ammonia production is at least in part resulting from controlling or reducing urease producing bacteria in the poultry litter and/or from the reduction or inhibition of urease enzymes in the poultry litter or poultry manure.

In some embodiments, the environment is improved by controlling or reducing pathogenic bacteria in the poultry litter or poultry manure.

In some embodiments, the environment is improved by controlling poultry litter pests, such as beetles and flies and their respective larvae.

In some embodiments, the improvement in the environment, improves feeding, laying, weight gain and other measures of productivity within the poultry facility.

In another aspect of the invention there is provided a method of preventing or reducing foot pad dermatitis (pododermatitis) and gangrenous dermatitis in the poultry in a poultry farming facility comprising applying to poultry litter within the poultry farming facility a composition comprising at least one microorganism of the genus *Bacillus* and at least one biosurfactant, wherein the biosurfactant is present in the composition in an amount of between about 2 mg/L and 7000 mg/L.

In some embodiments, the preventing or, reducing pododermatitis results from the control or reduction of *Staphylococcus* and or *Pseudomonas* microorganisms in the poultry litter. In some embodiments, the pododermatitis may be reduced or prevented by the reduction or lack of use of neutralizing acidic compounds in the poultry litter.

In another aspect of the invention, there is provided a composition comprising at least one microorganism of the genus *Bacillus* and at least one biosurfactant, wherein the biosurfactant is present in the composition in an amount of between about 2 mg/L and 7000 mg/L.

In some embodiments, the composition comprises 50 to 7000 mg/L of biosurfactant. In some embodiments, the composition is a concentrate which may be further diluted before use. In these embodiments, the biosurfactant may be present in an amount of 500 mg/L to 7000 mg/L, especially 800 mg/L to 7000 mg/L or 850 mg/L to 6000 mg/L. In some embodiments, the composition is in diluted form comprising biosurfactant in the range of 2 mg/L to 850 mg/L, especially 2 mg/L to 800 mg/L or 2 mg/L to 500 mg/L. In some embodiments, the composition further comprises a surfactant, especially an anionic surfactant.

In some embodiments, the composition comprises the *Bacillus* species RSA-203.

DETAILED DESCRIPTION OF THE INVENTION

1. Definitions

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "environment within a poultry farming facility" refers to the poultry housing areas of a poultry farming facility such as barns in which poultry are raised and/or where eggs are laid and include the floor or a storey of the barn, the poultry litter used in the barn, the air and air quality in the barn and the hard surfaces inside the barn.

As used herein, the term "poultry" refers to domesticated birds kept by humans for the purposes of obtaining eggs, meat and/or feathers. Poultry includes fowls, waterfowls and game birds. Examples of poultry include chickens, turkeys, ducks, geese, quail, pheasants, doves, pigeons, emus, ostriches and rhea.

As used herein, the term "vinasse" refers to a by-product of the sugar industry obtained from the processing of sugar cane or sugar beet. The molasses produced during sugar processing is fermented to produce ethanol and ascorbic acid. The residue left after this fermentation is referred to as vinasse. Vinasse is a viscous liquid with a total solids content of 2-10% w/v, high acidity pH 4-5 and high BOD (30 000-40 000).

2. Methods of the Invention

The invention relates to methods of improving the environment in a poultry facility, especially a mass production poultry facility. The methods comprising contacting poultry litter or poultry manure with a composition comprising at least one microorganism of the genus *Bacillus* and at least one biosurfactant, wherein the biosurfactant is present in the composition in an amount of between about 2 mg/L and 7000 mg/L. The methods may be used in poultry farms to control or reduce pathogenic bacteria, control or reduce the production of ammonia, treat or prevent poultry pododermatitis, or controlling or preventing pest infestation in poultry facilities. The composition also may improve productivity in poultry facilities.

The poultry farming facility may be a facility where poultry are produced for consumption or a facility where poultry are kept for their eggs, feathers or other poultry products.

In some embodiments, the methods are for controlling pathogenic bacteria in poultry litter or poultry manure. The pathogenic bacteria may be a gastrointestinal pathogen of poultry. The pathogenic bacteria may cause disease in the poultry, such as diarrhoea or pododermatitis. The pathogenic bacteria may also be pathogenic bacteria that infect humans. In some embodiments, the pathogenic bacteria are selected from *Salmonella* spp., *Clostridium* spp., *Campylobacter* spp., *Escherichia* spp. *Pseudomonas* spp. and *Staphylococcus* spp. For example, the pathogenic bacteria may be selected from *Salmonella enterica*, *Campylobacter jejuni*, *Staphylococcus aureus*, *Pseudomonas aeruginosa*, *Escherichia coli* and *Clostridium perfringens*. The bacteria may or may not have developed resistance to standard antibiotics or vaccines.

In another aspect of the invention there is a method of treating or preventing poultry pododermatitis or gangrenous dermatitis. Poultry pododermatitis also known as foot pad dermatitis, and gangrenous dermatitis are conditions that affect the feet of poultry that live in an environment covered with poultry litter. In some cases, the pododermatitis or gangrenous dermatitis is exacerbated by the presence of poultry litter amendments, such as neutralizing acids, that are used to control the production of ammonia in poultry litter, for example, alum, bisulfite salts and other acids. Poultry pododermatitis or gangrenous dermatitis may be caused by *Staphylococcus aureus* or *Pseudomonas aeruginosa* that is present in the poultry faecal matter that is present in the poultry litter. These conditions result in infection and blisters on the poultry bird's feet, hock burns and/or breast blisters.

In some embodiments, the methods are for controlling or reducing ammonia that is produced in poultry facilities. The ammonia is thought to be produced by hydrolysis of urea and uric acid that is in poultry faeces in the poultry litter or poultry manure. Hydrolysis of urea and uric acid to produce ammonia is accelerated by the presence of urease enzymes that are present in or excreted from bacteria in the poultry faeces. Without wishing to be bound by theory, it is believed the composition reduces urease enzyme activity in poultry feacal matter by controlling or killing the urease containing microbes in the feacal matter. Ureases catalyze the degradation of uric acid to ammonia within the feacal matter. Therefore in one aspect of the invention there is provided a method for controlling or inhibiting the activity of urease enzymes in the poultry litter or poultry manure.

In some embodiments, the ammonia concentration in the poultry facility is controlled to a level below 25 ppm, the maximum concentration of ammonia allowed in poultry facilities. In some embodiments, the concentration of ammonia as maintained below 20 ppm, 15 ppm or 10 ppm. Advantageously, the ammonia concentration may be maintained below 25 ppm for between 2 and 50 days, for example, 5 and 50 days, 10 and 50 days, 15 and 50 days, 20 and 50 days, especially a period of time sufficient for the poultry to grow from chicks to adults. Advantageously, maintaining the concentration of ammonia below 25 ppm reduces or eliminates the need for the use of ventilation fans in the facilities which are energy intensive and expensive to run.

In another aspect, the methods of the invention relate to controlling pests in the poultry litter. In particular embodiments, the pests are invertebrate pests such as insects. In one embodiment, the pest is selected from darkling beetles, especially darkling beetle larvae, and flies such as horse flies, little horse flies, black garbage flies, house flies, lesser house flies, stable flies, bottle flies, blow flies, fresh flies, drone flies and other domestic flies.

In yet another aspect of the invention, the method improves productivity of the poultry and poultry facility. The reduction in pathogenic bacteria and/or reduction of ammonia levels improves the general health of the poultry birds increasing their feeding and growth and producing healthy feet. The productivity increase may manifest itself by increased average weight of the poultry birds, the production of more eggs or larger eggs and/or the production of healthy saleable chicken feet for the Asian food market.

In some embodiments, the composition or diluted composition is sprayed over the poultry litter. In some embodiments, the composition is used neat. In other embodiments, the composition is diluted, for example, with water. However a bactericidal concentration of biosurfactant of at least 2 mg/L, especially 50 mg/L is maintained. In some embodiments, the composition is diluted by 1 part v/v composition in 2 parts water to 1 part v/v composition 30 parts water, for example, 1 part composition in 2 to 25 parts water, 1 part composition in 5 to 20 parts water, especially 1 part composition in 10 parts water, 1 part composition in 11 parts water, 1 part composition in 12 parts water, 1 part composition in 13 parts water, 1 part composition in 14 parts water, 1 part composition in 15 parts water, 1 part composition in 16 parts water, 1 part composition in 17 parts water, 1 part composition in 18 parts water, 1 part composition in 19 parts water or 1 part composition in 20 parts water.

When the composition of the invention is diluted, the composition may comprise about 1 to 40% v/v of the diluted composition, especially 1 to 30% v/v, 1 to 20% v/v, 1 to 15% v/v, 1 to 12% v/v or 1 to 10% v/v, more especially about 2 to 8%.

The composition, either diluted or undiluted, may be applied to the poultry litter in an amount of 1 gallon per 50 square feet to 1 gallon per 150 square feet (0.8 L/m$^2$ to 0.27 L/m$^2$), especially 1 gallon per 75 square feet to 1 gallon per 125 square feet (0.54 L/M$^2$ to 0.33 L/m$^2$) or 1 gallon per 90 square feet to 1 gallon per 120 square feet (0.45 L/m$^2$ to 0.34 L/m$^2$).

In some embodiments, the poultry litter comprises one or more of wood shavings, saw dust, straw, peanut husks, rice hulls, shredded sugar cane and other low cost dry, absorbent, low-cost organic materials. The type of organic material used may be dictated by local crops and their dry organic waste materials.

In some embodiments, the composition is applied to poultry litter between broods of poultry and therefore the litter comprises faecal matter prior to introduction of the next brood of chicks. The composition of the invention may be applied to the poultry litter 1 to 10 days before the introduction of the next brood of chicks, especially 3 to 7 days before.

In some embodiments, the composition is applied to poultry manure, for example, in egg producing facilities such as those containing caged poultry.

In some embodiments, the poultry litter or poultry manure may be subject to windrowing before or after application of the composition of the invention. In some embodiments, the composition applied to the windrow comprises microorganisms in spore form.

3. Compositions of the Invention

In one aspect of the present invention there is provided a composition comprising at least one microorganism of the genus *Bacillus* and at least one biosurfactant, wherein the biosurfactant is present in the composition in an amount of about 2 mg/L to 7000 mg/L.

In particular embodiments, the at least one microorganism from the genus *Bacillus* is a probiotic microorganism. In some embodiments, the composition comprises one microorganism from the genus *Bacillus*. In other embodiments, the composition comprises more than one microorganism from the genus *Bacillus*, for example 2, 3, 4, 5 or 6 microorganisms. In some embodiments, the at least one microorganism from the genus *Bacillus* is selected from *Bacillus subtilis, Bacillus licheniformis, Bacillus amyloliquejaciens, Bacillus pumilus, Bacillus popillae, Bacillus circulans* and mixtures thereof, especially *Bacillus subtilis* and *Bacillus licheniformis* and mixtures thereof, more especially *Bacillus subtilis*.

In some embodiments, the at least one microorganism from the genus *Bacillus* is a specific strain of *Bacillus subtilis*, especially *Bacillus subtilis* subspecies *subtilis* NRRL B-3383 (US Department of Agriculture, Agricultural Research Service, ARS Culture Collection NRRL), *B. subtilis* ATCC 21331, *B. subtilis* ATCC 21332, *B. subtilis* SD901 (FERM BP.7666), and *B. subtilis* RSA-203 or a mixture thereof. In some embodiments, the at least one microorganism of the genus *Bacillus* comprises *B. subtilis* RSA-203. In some embodiments, the at least one microorganism of the genus *Bacillus* is a combination of *Bacillus subtilis* NRRL B-3383 and *Bacillus subtilis* RSA-203.

RSA-203 is a microorganism that is a strain of *Bacillus subtilis*. It is a rod-shaped, aerobic, Gram-positive, β-hemolytic microbe capable of forming endospores. Nucleic acid sequence analysis confirms it is a strain of *B. subtilis*. A sample of this microorganism was deposited at ATCC depository, 10801 University Boulevard, Manassas, Va. 20110-2209, United States of America on 9 Jan. 2013, and has been allocated Accession No. PTA-13451.

RSA-203 produces significant amounts of the biosurfactant surfactin. If culture conditions include foamate removal during culture, surfactin may be produced in amounts of 250 mg/L to 1000 mg/L in the culture medium and 850 mg/L to 2 g/L in the foamate.

In some embodiments, the microorganism is in a vegetative state. In other embodiments, the microorganism is in a dormant state, for example, an endospore. In yet other embodiments, the microorganism is present in a mixture of dormant and vegetative states.

The composition may comprise any suitable amount of microorganism of the genus *Bacillus* to achieve a suitable population when applied to poultry litter. Without wishing to be bound by theory, the microorganism is thought to be able to take advantage of food sources in the poultry litter more effectively than other microorganisms such as pathogenic bacteria. This results in the microorganisms of the genus *Bacillus* outperforming the other microorganism, such that the other microorganisms do not thrive or die. Suitable amounts of microorgansism of the genus *Bacillus* are between $1 \times 10^4$ cfu/mL to $1 \times 10^{13}$ cfu/mL.

In some embodiments, the at least one biosurfactant is produced by the microorganism of the genus *Bacillus* that is in the composition. In other embodiments, the at least one biosurfactant is not produced by the microorganism of the genus *Bacillus* that is in the composition.

In some embodiments, the at least one biosurfactant is an antimicrobial peptide, especially a cyclic lipopeptide biosurfactant. In some embodiments, the biosurfactant is one of surfactin, lichenysin, iturin, fengycin or mixtures thereof, more especially surfactin, lichenysin or mixtures thereof, most especially surfactin. Each of these biosurfactants may contain mixtures of compounds, varying in chain length of the fatty acid moiety of the lipopeptide.

Cyclic lipopeptides, such as surfactin, have a cyclic peptide moiety and a moiety derived from a fatty acid. Surfactin has a cyclic peptide of seven amino acids including both D- and L-amino acids, Glu-Leu-D-Leu-Val-Asp-D-Leu-Leu, linked from the N-terminus to the C-terminus to form a cyclic moiety by a $C_{12}$-$C_{17}$ β-hydroxy fatty acid as shown below.

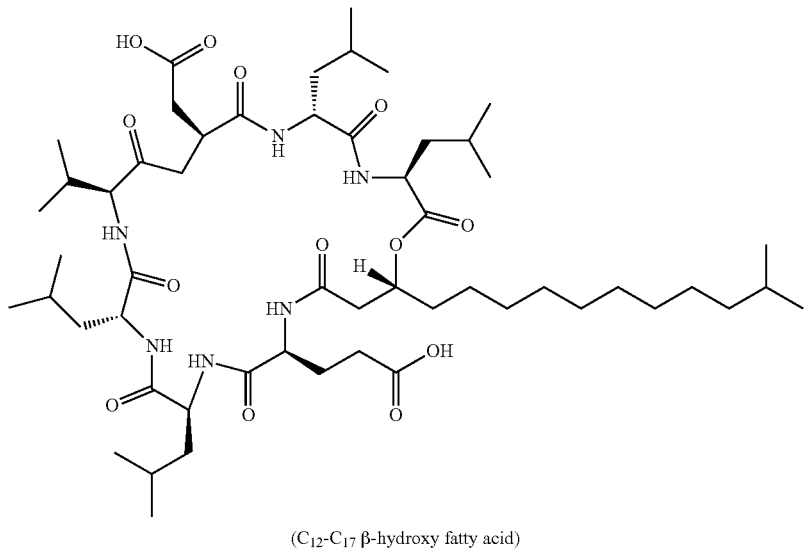 [SMILES: CC(C)CCCCCCCCC[C@@H]1CC(=O)N[C@@H](CCC(=O)O)C(=O)N[C@@H](CC(C)C)C(=O)N[C@H](CC(C)C)C(=O)N[C@@H](C(C)C)C(=O)C[C@@H](CC(=O)O)C(=O)N[C@H](CC(C)C)C(=O)N[C@@H](CC(C)C)C(=O)O1 ; "(C12-C17 b-hydroxy fatty acid)"]

($C_{12}$-$C_{17}$ β-hydroxy fatty acid)

Lichenysin has a similar structure with the amino acid sequence differing from surfactin, Gln-Leu-D-Leu-Val-Asp-D-Leu-Ile, linked from the N-terminus to the C-terminus to form a cyclic moiety by a $C_{12}$-$C_{17}$ β-hydroxy fatty acid.

Fengycin is a cyclic lipopeptide having the sequence Glu-D-Orn-Tyr-D-Allo-Thr-Glu-D-Ala-Pro-Glu-D-Tyr-Ile where the peptide is cyclized between the tyrosine phenoxy group of position 3 and the C-terminus of the Ile at position 10, the fatty acid is attached to the peptide forming an amide with the N-terminus.

Iturin refers to a group of cyclic peptides with the sequence Asn-D-Tyr-D-Asn-Gin-Pro-D-Asn-Ser in which the N-terminus and C-terminus are connected by a β-amino fatty acid of varying length.

The composition comprises biosurfactant in an amount of 2 mg/L to 7000 mg/L, for example 50 mg/L to 7000 mg/L. In some embodiments, the composition is in the form of a concentrate that may be diluted before use. For example, the concentrate may comprise biosurfactant at a concentration of 500 mg/L to 7000 mg/L, 800 mg/L to 7000 mg/L or 850 mg/L to 6000 mg/L. In some embodiments, the composition is in diluted form and comprises biosurfactant in the range of 2 mg/L to 850 mg/L, especially 2 mg/L to 800 mg/L or 2 mg/L to 500 mg/L. In some embodiments the composition comprises biosurfactant in an amount of about 50 mg/L to 4000 mg/L, 50 mg/L to 2000 mg/L, 100 mg/L to 2000 mg/L, 400 mg/L to 2000 mg/L or about 750 mg/L to 1500 mg/L.

The composition comprises an aqueous carrier, for example, water, buffer or culture broth. In some embodiments, the aqueous composition is buffered at a pH from 3 and 8. For example, citric acid buffer can be used to maintain a pH of 3 to 6 or a phosphate buffer such as monosodium phosphate, monopotassium phosphate, disodium phosphate or dipotassium phosphate may be used to maintain a pH of from 4.8 to 8. In some embodiments, the composition has a pH of from 3 to 6. In other embodiments, the composition has a pH of 6 to 8.

In some embodiments, the composition further comprises at least one surfactant. The surfactant may be anionic, cationic, non-ionic or zwitterionic. In some embodiments, the surfactant has a Hydrophilic Lipophilic Balance (HLB) of 12 or greater, especially in the range of 12 to 14. Suitable surfactants include those referred to in McCutcheon's Emulsifiers & Detergents, International Edition, 1998 and subsequent Editions, for example those referred to at pages 223 to 231 of the HLB index of the 1998 Edition. Exemplary non-ionic surfactants include alkyl and polyalkyl esters of poly(ethylene oxide), alkyl and polyalkyl ethers of poly(ethylene oxide), alkyl and polyalkyl esters of sorbitan optionally polyethoxylated, alkyl and polyalkyl ethers of sorbitan optionally polyethoxylated, alkyl and polyalkyl glycosides or polyglycosides, in particular alkyl and polyalkyl glucosides or polyglucosides, alkyl and polyalkyl esters of sucrose, alkyl and polyalkyl esters of glycerol optionally polyethoxylated, alkyl and polyalkyl ethers of glycerol optionally polyethoxylated, and mixtures thereof. Exemplary anionic surfactants include alkyl ether sulphates, carboxylates, derivatives of amino acids, sulfonates, such as linear alkylbenzene sulfonates, or sulfonic acids, isothionates, taurates, sulphosuccinates, alkylsulphoacetates, polypeptides, metal salts of $C_{10}$-$C_{30}$, notably $C_{12}$-$C_{20}$ fatty acids, in particular metal stearates, and mixtures thereof. In a particular embodiment, the surfactant is a linear alkylbenzenesulfonate or sulfonic acid, especially dodecylbenzenesulfonic acid.

Suitable alkyl and polyalkyl esters of poly(ethylene oxide) include those having a number of ethylene oxide (EO) units ranging from 2 to 200, for example, stearate 40 EO, stearate 50 EO, stearate 100 EO, laurate 20 EO, laurate 40 EO, distearate 150 EO. Suitable alkyl and polyalkyl ethers of poly(ethylene oxide) include those having number of ethylene oxide (EO) units ranging from 2 to 200, for example, cetyl ether 23 EO, oleyl ether 50 EO, phytosterol 30 EO, steareth 40, steareth 100, beheneth 100. Suitable alkyl and polyalkyl esters of sorbitan optionally polyethoxylated, include those having number of ethylene oxide (EO) units ranging from 0 to 100, for example, sorbitan laurate 4 or 20 EO, in particular polysorbate 20 (or polyoxyethylene (20) sorbitan monolaurate) such as the product Tween 20 marketed by the company Uniqema, sorbitan palmitate 20 EO, sorbitan stearate 20 EO, sorbitan oleate 20 EO or Cremophor (RH 40, RH 60 etc.) from BASF. Suitable alkyl and polyalkyl ethers of sorbitan, optionally polyethoxylated, include those having number of ethylene oxide (EO) units ranging from 0 to 100. Suitable alkyl and polyalkyl glucosides or polyglucosides, include those containing an alkyl group having from 6 to 30 carbon atoms and especially from 6 to 18, or even from 8 to 16 carbon atoms, and containing a glucoside group, especially containing from 1 to 5, notably 1, 2 to 3 glucoside units. The alkylpolyglucosides can be selected for example from decylglucoside (Alkyl-Cg/Cn-polyglucoside (1.4)) such as the product marketed under the name Mydol 10® by the company Kao Chemicals or the product marketed under the name Plantacare 2000 UP® by the company Henkel and the product marketed under the name ORAMIX NS 10® by the company SEPPIC; caprylyl/capryl glucoside such as the product marketed under the name Plantacare KE 3711® by the company Cognis or ORAMIX CG 110® by the company SEPPIC; laurylglucoside such the product marketed under the name Plantacare 1200 UP® by the company Henkel or Plantaren 1200 N® by the company Henkel; cocoglucoside such as the product marketed under the name Plantacare 818 UP® by the company Henkel; caprylylglucoside such as the product marketed under the name Plantacare 810 UP® by the company Cognis; and mixtures thereof. Suitable alkyl and polyalkyl esters of sucrose include, for example Crodesta F 150, sucrose monolaurate marketed under the name Crodesta SL 40, and the products marketed by Ryoto Sugar Ester for example, sucrose palmite marketed under reference Ryoto Sugar Ester P 1670, Ryoto Sugar Ester LWA 1695, and Ryoto Sugar Ester 01570. Suitable alkyl and polyalkyl esters of glycerol optionally polyethoxylated, include those having number of ethylene oxide (EO) units ranging from 0 to 100 and number of glycerol units ranging from 1 to 30, for example, hexaglyceryl monolaurate and PEG-30 glyceryl stearate. Suitable alkyl and polyalkyl ethers of glycerol optionally polyethoxylated, include those having number of ethylene oxide (EO) units ranging from 0 to 100 and number of glycerol units ranging from 1 to 30. Examples include Nikkol Batyl alcohol 100, Nikkol chimyl alcohol 100. Suitable alkyl ether sulphates include, for example lauryl ether sodium sulphate (C12-14 70-30) (2.2 EO) marketed under the names SIPON AOS225 or TEXAPON N702 by the company Henkel, lauryl ether ammonium sulphate (C12-14 70-30) (3 EO) marketed under the name SIPON LEA 370 by the company Henkel, alkyl (C12-C14) ether (9 EO) ammonium sulphate marketed under the name RHODAPEX AB/20 by the company Rhodia Chimie, and the mixture of lauryl and ether sulphate of sodium and of magnesium marketed under the name EMPICOL BSD 52 by the company Albright & Wilson.

The surfactant may be present in an amount to assist with wetting of the poultry litter when the composition is applied. Suitable amounts include 0.01 to 10% wt/wt, especially 0.1% to 5% wt/wt, more especially 0.1 to 1% wt/wt of the composition.

In some embodiments, the composition further comprises an organic acid. In some embodiments, the organic acid is selected from citric acid, acetic acid, lactic acid, tartaric acid, ascorbic acid and the like, especially citric acid. The organic acid is included to adjust the pH to between 3 and 6 and may assist in neutralizing free ammonia in the poultry litter which is present when the composition is applied to the litter or that is produced after application of the composition to the poultry litter.

Other optional components of the composition include fragrances such as citrus oil extract and the like. Such fragrances may be synthetic or natural but are preferably natural; and dyes, which may be useful in identifying treated poultry litter. Suitable dyes include food grade dyes such as FD&C Green #5, FD&C Green #3, FD&C Blue #1, FD&C Blue #2, FD&C Red #40, FD&C Red #3, FD&C Yellow #5, FC&C #6, Green S, Quinoline Yellow, Carmoisine, Ponceau 4R, Patent Blue V, annatto, chlorophylin, cochineal, betanin, saffron, tumeric, lycopene, elderberry juice, pandan and butterfly pea.

The composition of the invention may be prepared in a microbial culture. The microorganism from the genus *Bacillus* may be produced by standard culture techniques. For example, a bioreactor is charged with demineralized water salts and nutrients and mixed. The culture medium is then inoculated with a culture of the desired microorganism. The biomass is then aerated, agitated and incubated at a suitable temperature, for example, 35° C., until the desired microbial growth is obtained. The desired microbial growth may be determined by optical density at 600 nm ($OD_{600\ nm}$). In particular embodiments, the culture is continued until the optical density reaches $OD_{600\ nm} > 1.5$ to 2.5, especially 1.7 to 2.0.

An exemplary process includes charging a bioreactor with demineralized water, monopotassium phosphate, disodium phosphate, ammonium nitrate, yeast extract, magnesium sulphate, calcium chloride, ferrous sulphate, manganese sulphate, sodium ethylene diamine tetraacetic acid (EDTA) and glucose. After mixing, the culture medium is inoculated with an appropriate *Bacillus* sp. The culture is then aerated and agitated at 300 rpm for about 12 hours at 35° C. The culturing process was complete when the cell density reached $1 \times 10^{14}$ colony forming units (cfu) per mL or $OD_{600\ nm}$ between 1.7 and 2.0.

While in some embodiments, the composition may comprise the culture medium containing microorganism and biosurfactant in sufficient quantities produced directly from the culture process. In other embodiments, the biosurfactant is added to the culture medium or a composition comprising the microorganism in vegetative or endospore state.

In some embodiments, the culture process may be performed using *Bacillus* microorganisms that do not produce sufficient amounts of biosurfactant to use in the invention. In some embodiments, the culture process includes the step of continuous removal of biosurfactant by foam distillation thereby encouraging the microorganism to produce larger amounts of biosurfactant by depleting the biosurfactant as it is produced. In yet other embodiments, the microorganism of the genus *Bacillus* is isolated, for example, in endospore form, and is not in culture medium and therefore does not contain biosurfactant. In these embodiments, a desired amount of biosurfactant may be added to the microorganism to form a composition of the invention.

The biosurfactant may be produced as described above or by other methods known in the art. The production of biosurfactants, such as surfactin, are described in the literature, for example in U.S. Pat. No. 3,687,926, JP-A-6-121668, U.S. Pat. Nos. 3,030,789, 7,011,969, Wei et al. *Enz. Microbiol. Technol.*, 1989, 22:724-728, Sheppard et al., *Appl. Microbiol. Biotechnol.*, 1989, 27:486-489, Mulligan et al., *Appl. Microbiol. Biotechnol.*, (1989), 31:486-489, Kim et al. *J. Ferment. Bioeng.*, 1997, 84:41-46 and Cooper et al., *Appl. Environ. Microbiol.*, 1981, 42:408-412.

In particular embodiments, the microorganism of the genus *Bacillus* in the composition is a biosurfactant-producing microbe.

The biosurfactant may be produced by any biosurfactant-producing microbe. However, in particular embodiments, the at least one biosurfactant-producing microbe is from the genus *Bacillus*, for example, they may be selected from *Bacillus subtilis, Bacillus licheniformis, Bacillus amyloliquefaciens, Bacillus pumilus, Bacillus popilliae, Bacillus circulans* and mixtures thereof. In some embodiments, one biosurfactant-producing microbe is present in the liquid culture medium. In other embodiments, two biosurfactant-producing microbes are present in the liquid culture medium. In yet another embodiment, three biosurfactant-producing microbes are present in the liquid culture medium. In still further embodiments, four biosurfactant-producing microbes are present in the liquid culture medium. In some embodiments, the at least one biosurfactant-producing microbe is a mixture of five biosurfactant-producing microbes. The at least one biosurfactant-producing microbe may be a strain of microbe known to produce biosurfactants in improved yields. For example, many species of *Bacillus* produce biosurfactants, however, *Bacillus subtilis* and *Bacillus licheniformis* are known to produce significant quantities of biosurfactants. Furthermore, specific strains of *Bacillus subtilis* are known to produce improved yields of biosurfactants such as *B. subtilis* ATCC 21331, *B. subtilis* ATCC 21332, *B. subtilis* SD901 (FERM BP.7666). Many strains of biosurfactant-producing microbes are commercially or publicly available. In particular embodiments, the at least one biosurfactant-producing microbe is selected from *B. subtilis* NRRL B-3383 or *B. subtilis* ATCC 21331 both of which are publicly available. In other embodiments, the biosurfactant-producing microorganism is *B. subtilis* RSA-203, a new strain of *B. subtilis* found to produce significant yields of the biosurfactant, surfactin.

In some embodiments, the at least one biosurfactant-producing microbe is a mixture of *B. subtilis* and *B. licheniformis*. In other embodiments, the at least one biosurfactant-producing microbe is a mixture of *B. subtilis, B. licheniformis, B. amyloliquefaciens, B. pumilus* and *Bacillus popilliae*. In these embodiments, the ratio of each microbe may be adjusted to determine the amount of different biosurfactants produced. In some embodiments, the *B. subtilis* is present in a mixture of biosurfactant-producing microbes in about 50-98% of the mixture, especially 60-95%, 70-95%, 80-95%, more especially about 90%.

In some embodiments, the carbon source used in the liquid culture medium is a sugar or carbohydrate. Examples of suitable carbon sources include glucose, glycerine, starch, sucrose, molasses and vinasse or mixtures thereof. In some embodiments, the carbon source comprises glucose. In other embodiments, the carbon source comprises vinasse.

In some embodiments, the amount of carbon source, such as glucose, molasses and/or vinasse, in the liquid culture medium is from 3-20% w/v, especially 3-15% w/v, more especially 3-12% w/v or 3-10% w/v, most especially about 10% w/v. In some embodiments, the amount of carbon source is varied to obtain a desired concentration of biosurfactant in the culture broth.

The biosurfactant produced is preferably a cyclic lipopeptide biosurfactant such as surfactin, lichenysiri, iturin, fengycin and mixtures thereof. Each of these biosurfactants may contain mixtures of compounds varying in the chain length of the fatty acid moiety of the lipopeptide. The modulation of growth conditions and nutrients enables the production of biosurfactants with varying ratios of lipid fatty acid chain lengths.

In some embodiments, the biosurfactant produced is selected from surfactin and lichenysin and mixtures thereof. In other embodiments, the biosurfactant produced is surfactin.

The temperature of the culturing process is 25° C. to 40° C., especially 30° C. to 40° C., more especially about 30° C. to 35° C., for example 32° C. to 35° C. The temperature used may depend on the identity of the biosurfactant-producing microbe. A person skilled in the art could determine appropriate temperature for a given bacterial population by routine trial methods.

The pH of the culture medium is maintained between 4 and 8, especially 6 and 8, or 6 and 7.5, more especially 6.3 to 7.2, for example 6.3 to 6.7.

The inoculum of at least one biosurfactant-producing microbe is added to the culture medium in an amount of to achieve an initial $OD_{600\ nm}$ equal to 0.1 to 0.15. In some embodiments, the inoculum is a culture having an $OD_{600\ nm}$ of 1.3 to 2.5. In some embodiments, the inoculum is a culture in mid-log phase growth with an $OD_{600\ nm}$ of 1.3 to 1.6 and is added to the new culture in an amount to achieve an $OD_{600\ nm}$ of 0.1 to 0.15. The amount required may be readily calculated, for example, inoculums with $OD_{600\ nm}$ of 1.5 will be added in 10% v/v ratio to obtain a new culture medium with an $OD_{600\ nm}$ of 0.15.

In some embodiments, the liquid culture medium further comprises a catabolizable nitrogen source. In some embodiments, the catabolizable nitrogen source is selected from a nitrogen containing inorganic salt or nitrogen-containing organic compound for example, ammonium salts, nitrate salts, urea, peptone, meat extract, yeast extract, soybean cake, corn steep liquor, peptone, or flour derived from legumes such as soybean, adzuki bean, pea, broad bean, chick pea, lentil and string bean or extracts of such a flour or mixtures thereof. In particular embodiments, the catabolizable nitrogen source is an inorganic salt such as an ammonium salt or nitrate salt, especially ammonium nitrate, ammonium chloride, ammonium acetate, ammonium carbonate, ammonium bicarbonate, potassium nitrate, sodium nitrate, magnesium nitrate, and calcium nitrate or mixtures thereof. In particular embodiments, the catabolizable nitrogen source is ammonium nitrate, sodium nitrate, ammonium chloride or mixtures thereof, for example, sodium nitrate, ammonium nitrate or a mixture thereof.

The amount of catabolizable nitrogen source present in the liquid culture medium will depend on the nature of the source and the availability of the nitrogen within the source. For example, the nitrogen source may be present in an amount of 1 to 20 g/L. When the nitrogen source is an inorganic nitrogen source, it may be present in an amount of 1 to 10 g/L, especially 2 to 7 g/L, more especially 3.5 to 4.5 g/L.

In some embodiments, the liquid culture medium further comprises at least one inorganic salt, such as sulfates, phosphates, chlorides, especially of metals such as manganese, iron, sodium, potassium, magnesium and calcium. In some embodiments the inorganic salts are selected from sulfates and phosphates of ions such as manganese, magnesium, sodium, potassium and iron or mixtures of such salts. In particular embodiment, the at least one inorganic salt is selected from manganese sulfate, sodium phosphate, calcium chloride, magnesium sulfate, ferrous sulfate and mixtures thereof, especially sodium phosphate, manganese sulfate and ferrous sulfate or mixtures thereof.

The inorganic salts vary in amount depending on the salts used. If a source of phosphate is present, it may be present in an amount of about 1 to 10 g/L, especially 2 to 7 g/L, more especially 4 to 7 g/L, most especially 5 to 6 g/L. Where inorganic salts are added to provide trace elements such as iron, manganese, and calcium, the amounts will vary between 1 mg/L and 5 g/L, for example, calcium salts may be added in an amount of 0.5 g/L to 1 g/L, iron salts may be added in an amount of 1 to 10 mg/L, manganese salts may be added in an amount of 0.5 to 1 g/L, magnesium salts may be added in an amount of 0.5 g/L to 5 g/L.

In some embodiments, the culture medium further comprises a chelating agent. Particular chelating agents include amino carboxylic acids and salts thereof, such as ethylene diamine tetraacetic acid (EDTA), diethylenetriamine pentaacetic acid, hydroxyethylethylenediamine triacetic acid, 1,2-diamino-cyclohexane tetraacetic acid, ethylene glycol-bis([beta]-aminoethyl ether)-N,N,N',N'-tetraacetic acid (EGTA), diethylenetriamine-pentaacetic acid (DPTA), triethylenetetraamine hexaacetic acid (TTG), aminodiacetic acid and hydroxyethyl aminodiacetic acid. Particular chelating agents are salts and mixed salts of EDTA such as dipotassium, ammonium, calcium, disodium, trisodium and tetrasodium salts, most preferably disodium or tetrasodium salts of EDTA, especially disodium EDTA. The chelating agent is present in amount of between 0.1 and 5 mg/L, especially 0.5 to 3 mg/L, more especially 1 to 2.5 mg/L of culture medium.

The culturing method may occur on a small scale in laboratory flasks in an incubator or may occur on larger scale, such as industrial scale in a bioreactor. The method is conducted under aerobic conditions.

The duration of the culturing process will depend on the culture conditions. In some embodiments, the culturing process has a duration of 8 to 120 hours, especially 8 to 72 hours, 8 to 48 hours or 8 to 24 hours, for example, 10 to 14 hours. The duration of the culturing process is dependent of achieving a cell density greater than $OD_{600\ nm}$ of 1.3 for surfactin production.

In some embodiments, the process further comprises aeration of the culture medium to provide dissolved oxygen. Typically, this involves bubbling air through the culture medium at a rate of between 1 L/minute to 3 L/minute, especially about 1.5 L/minute. The rate of aeration may readily be determined by a person skilled in the art. Aeration may occur from the beginning of the culturing process or may begin after the culturing process has begun, especially from the beginning of the culturing process. In particular embodiments, aeration maintains a dissolved oxygen concentration of about 20 to 40%, especially 25 to 35%. In some embodiments, the dissolved oxygen concentration is maintained at about 30%.

Once biosurfactant production has begun, the culture medium may foam because of the presence of biosurfactant. In some embodiments, the foam production may be controlled by spraying the foamate with a mixture of alcohol such as ethanol and solvent such as dimethylene chloride or acetone. In some embodiments, the bioreactor in which the fermentation is done is explosion proof. In some embodiments, the foam collecting equipment is explosion proof. The extent of pressure for which equipment must withstand is determined by the pump pressure and flow rate into the foam column.

In some embodiments, the production of foamate is encouraged and the foamate is collected from the culturing vessel. The foamate comprises the biosurfactant produced. The foam may be collected via a rotary valve into a tank with a slight vacuum or a tank with a spray column to break the foam. The biosurfactant may be isolated from the foamate collected. In some embodiments, the biosurfactant is isolated by acidification followed by liquid/liquid extraction and then evaporation of the liquids.

In other embodiments, the biosurfactant is isolated from the culture medium after the culturing process is complete. For example, the crude culture medium may be centrifuged to remove biomass. The supernatant is then acidified to acidic pH, for example, pH 2 with acid, such as HCl. The acidic pH results in the precipitation of the biosurfactant, the acidified supernatant may be stood at 4° C. for a period of time to ensure precipitation is complete. The precipitate is then collected, for example, by centrifugation or filtration and resuspended in water. The pH of the suspension is adjusted to alkaline pH such as pH 8 to solubilize the precipitate. The resulting aqueous solution may be extracted with an organic solvent such as dichloromethane, ethyl acetate, chloroform, especially dichloromethane, and the organic phase evaporated to give the biosurfactant in high purity crystalline form. In some embodiments, the biosurfactant may be collected by foam distillation during culturing or after culturing is complete. The biosurfactant collected or isolated may be added to other cultures or compositions comprising microorganisms of the genus *Bacillus*, especially where the microorganism is in endospore form. This allows the composition of the invention to have a higher concentration of biosurfactant than could normally be obtained from or tolerated by the microorganism.

The composition of the invention may be prepared by adding biosurfactant to a composition comprising the microorganism to provide biosurfactant in an amount between 2 mg/L to 7000 mg/L. In some embodiments, the microorganism is in culture medium. In other embodiments, the microorganism is in water, especially deionized water. In some embodiments, the microorganism is in culture broth and is diluted with water, especially deionized water.

In some embodiments, where the biosurfactant producing microorganism is a microorganism from the genus *Bacillus*, the culturing of the microorganism for use in the composition also produces the biosurfactant. Therefore at least one biosurfactant in the microorganism and composition may be produced in a single step. In this embodiment, the composition may comprise culture medium and biosurfactant. In this embodiment, if increased biosurfactant is required, further biosurfactant may be added.

In some embodiments, at least some of the microorganism of the genus *Bacillus* in the composition is in spore form. At this time, surfactant as described above may also be added.

In some embodiments, the culture broth from concurrent production of microorganism of the genus *Bacillus* and biosurfactant is diluted and endospores form by addition of the culture broth to a mixture of water, pH adjuster such as sodium hydroxide, monopotassium phosphate or citric acid, and surfactant.

In some embodiments, after endospore formation, additional biosurfactant is added to the composition, for example, in amounts of 100 to 1000 mg/L, especially about 400 to 750 mg/L.

The composition of the invention comprises the microorganism in any suitable amount, however, in some embodiments, the microorganism is present in an amount of about $1\times10^4$ cfu/mL to $1\times10^{13}$ cfu/mL.

In another aspect of the invention there is provided a microbe *Bacillus subtilis* RSA-203.

The invention will now be described with reference to the following examples which illustrate some preferred aspects of the invention. However, it is to be understood that the particularity of the following description of the invention is not to supersede the generality of the preceding description.

BRIEF DESCRIPTION OF THE FIGURE

FIG. 1 is a graphical representation showing the growth of microorganisms over time with varying amounts of sulfate ions.

EXAMPLES

Example 1: Production of Surfactin Biosurfactant

*Bacillus subtilis* NRRL B-3383 strain (originally obtained from the United States Department of Agriculture) from bacterial culture was transferred at a 2% volume by volume inoculum into 4 L shake flasks containing 2.5 L of 10% vinasse based MMS broth. The vinasse based MMS broth containing:

| component | quantity |
| --- | --- |
| vinasse | 100 mL |
| ammonium nitrate | 4.1 g |
| sodium phosphate dibasic | 5.68 g |
| tetrasodium tetrahydrate EDTA | 1.8 mg |
| manganese sulfate | 6.8 mg |
| autoclaved deionized water | to 1 L |

The flasks were placed on orbital shakers (SKC 6100, Jeio Tech) at 150 rpm while incubating at 30° C. (MCO-801C Incubator, Sanyo). After 72 hours, flasks were removed from the incubator and the biomass removed from the crude culture broth by centrifugation at 8,500 rpm for 20 min at 4° C. (Sorvall Evolution RC).

The pH of the resulting supernatant was brought to a pH of 2.0 using HCl which resulted in precipitation of surfactin arid the supernatant stored overnight at 4° C. to ensure complete precipitation. The precipitate was collected by centrifugation at 8,500 rpm for 20 minutes at 4° C. Approximately 2.5 g/L of crude material was collected in the pellet. The pellet was suspended in deionized water and the pH adjusted to 8.0 using 1 M NaOH. The aqueous solution was extracted with an equal volume of dichloromethane. The dichloromethane layer was separated and allowed to evaporate to provide purified crystalline surfactin in an amount of 50 mg/L to 750 mg/L.

The samples of crystalline surfactin were examined for purity against a standard composition of pure surfactin (Sigma Aldrich, 98% pure). Analysis of the standard composition by LC-MS showed peaks with retention times at 1.03, 1.23, 1.61, 1.74, 2.15 and 2.93 minutes. Purity was calculated based on peak area.

Four samples tested for purity using the above method were found to be 80%, 56%, 58% and 61% pure.

Example 2: Production of Blends of Surfactin and Lichenysin

*Bacillus subtilis* and *Bacillus licheniformis* were used to inoculate 4 L shake flasks containing 10% molasses based MMS broth. The molasses based MMS broth containing:

| component | quantity |
| --- | --- |
| molasses | 100 mL |
| ammonium nitrate | 4.1 g |
| sodium phosphate dibasic | 5.68 g |
| tetrasodium tetrahydrate EDTA | 1.8 mg |
| manganese sulfate | 6.8 mg |
| autoclaved deionized water | to 1 L |

The flasks were placed on orbital shakers (SKC 6100, Jeio Tech) at 150 rpm while incubating at 30° C. (MCO-801C Incubator, Sanyo). After 72 hours, flasks were removed from the incubator and the biomass removed from the culture broth by centrifugation at 8,500 rpm for 20 min at 4° C. (Sorvall Evolution RC).

Example 3

In a 1 liter bioreactor a buffer solution was prepared containing 800 mL demineralized water, monopotassium phosphate (20.4 g), disodium phosphate (28.4 g) and yeast extract (5 g). The buffer was mixed and the pH adjusted to 7. The buffer was then autoclaved. In a 1 L bioreactor, 200 mL of the buffer solution was mixed with magnesium sulfate (2 mL of 12 g/100 mL solution), calcium chloride (1 mL, 0.1

M), ferrous sulfate heptahydrate (1 mL, 15.7 g/100 mL solution), manganese sulfate monohydrate (1 mL, 3.8 g/100 nil solution), sodium EDTA (1 mL, 0.18 g/100 mL solution) and glucose (20 mL, 20 g/80 g deionized water) and ammonium nitrate (10 mL, 82 g/200 mL solution). *Bacillus* species spores were inoculated into the bioreactor at 2% wt. The biomass was agitated at 300 rpm for 12 hours at 35° C. The *Bacillus* was incubated until the cell density was to $1 \times 10^{14}$ cfu per mL and the $OD_{600\ nm}$ was 2.2.

Example 4: Coproduction of *Bacillus* Species and Biosurfactant 2200 lbs (998 kg) of demineralized water was added to a 560 gallon (2200 L) stainless steel reactor and warmed to 35° C. 8.7 lbs (3.95 kg) of monopotassium phosphate and 13.3 lbs (6 kg) of disodium phosphate were added and the composition mixed. Magnesium sulfate (240 g), calcium chloride (33 g), EDTA (2.2 g) dissolved in 100 mL of water, ferrous sulfate (104 g), manganese sulfate (41.7 g), dextrose monohydrate (10.7 lbs, 4.85 kg), autoclaved yeast extract (2.14 lbs, 0.97 kg), ammonium chloride (6.1 lbs, 2.77 kg) and sodium nitrate (9.6 lbs, 4.35 kg) were added and mixing was continued at a temperature of 35° C. 23 L of *Bacillus* innoculum having an $OD_{600\ nm}$ of 2.2 and a surface tension greater than 50 dynes/cm was added. The mixture was mixed and maintained at 35° C. and aerated to a dissolved oxygen level of 50% with filtered air. The culture was stopped when the culture medium reached an optical density of 1.7 to 2.0 Absorbence units.

Example 5: Composition

A composition for use in the methods of the invention was then prepared by further dilution of the culture medium produced in Example 4. In a 1000 gallon stainless steel dilution reactor was added 2200 lbs (998 kg) of demineralized water and monosodium phosphate (5 lbs, 2.27 kg) was added with agitation. Sodium hydroxide (5-60 lbs, 2.27-27.2 kg) and <1% wt non-ionic dodecylbenzenesulfonic acid was added. The pH was adjusted to 6-8 with sodium hydroxide. The cultured bacteria and medium were then added and the composition mixed. Surface tension was checked and additional concentrated surfactin foam condensate was added to provide a surface tension of 27-35 dynes/cm.

Example 6: Composition

The method of Example 5 was repeated with the exception that the pH was adjusted to 3.5 to 5 with citric acid.

Example 7: Ammonia Production in Chicken Litter

Chicken litter containing chicken faeces was divided into two cubic yard boxes in equal amounts. One box was monitored for ammonia production without, further treatment (control). The other box was treated by spraying the chicken litter with a composition comprising microbes of the *Bacillus* species including *B. subtilis*, vinasse residue and surfactin. The composition was derived from culturing process and diluted to 5-25% per litre with water and the litter was treated at a rate of 1 L per 100 square metres.
Results:
The control box had an ammonia concentration of 20 ppm. The treated box had an ammonia concentration of 8 ppm.

Example 8: Ammonia Production in Poultry Barns

Four poultry barns (broilers), each having an area of 22,000 square feet (2044 m$^2$) and housing 22,300 birds were used. In all four houses, the poultry litter was treated 5 days before the placement of poultry chicks in the barn.

Barn One was treated with the composition of Example 4. 12.5 (47.3 L) gallons of the composition of Example 5 was mixed with 185 gallons (700 L) of water then blended and sprayed on the poultry litter comprising sawdust and compost in half the barn. This process was repeated with another 12.5 gallons (47.3 L) of composition in 185 gallons (700 L) of water to treat the other half of the barn.

Barn Two was treated with the composition of Example 5. 12.5 gallons (47.3 L) of the composition of Example 5 was mixed with 185 gallons (700 L) of water then blended and sprayed on the poultry litter in half the barn. This process was repeated with another 12.5 gallons (47.3 L) of composition in 185 gallons (700 L) of water to treat the other half of the barn.

Barns Three and Four were treated with aluminium bisulphate, a pH adjustment substance. In each barn, 1650 pounds (748 kg) of aluminium bisulphate was blended in 500 gallons (1893 L) of water, and sprayed on the poultry litter.

In each barn the aqueous treatment was applied by a motorized 6 nozzle sprayer equipped with and fed from a 200 gallon (757 L) tank, mounted on a four wheeled vehicle. After application, the poultry litter was windrowed by tractor.

After treatment three samples of litter were taken from each of the Barns and analysed for ammonia gas.

The poultry chicks were placed in the barns and air samples were taken at days 1, 5, 16, 21 and 39 and analysed for ammonia concentrations using Drager tubes (Drager Safety Inc., Pittsburgh, Pa. USA). The results are shown in Table 1.

TABLE 1

|  | Day one | Day five | Day sixteen | Day twenty one | Day 39 |
| --- | --- | --- | --- | --- | --- |
| Barn One | 10 | 10 | 20 | 20 | 12 |
| Barn Two | 10 | 10 | 20 | 20 | 15 |
| Barn Three | 0 | 20 | 18 | >25 | Full fans |
| Barn Four | 0 | 20 | 18 | >25 | Full fans |

Full fans indicates that mechanical ventilation of the barn was required to control ammonia concentrations.

The poultry in all four barns were assessed for health, morbidity and weight. The poultry in all four barns were in good health.

The feet of the poultry were analysed by paw grading; healthy paws graded as 1, through to infected and blistered paws graded as 4. In Barns One and Two the paw grading was 1. No birds had blisters on their feet.

Morbidity levels in Barns One and Two was reduced by an average of 133 birds compared to Barns Three and Four.

Bird weights increased in Barns One and Two by 15 to 20 points compared to Barns Three and Four. This equates to a total of 11,000 lbs of additional weight in 35 days in Barns One and Two.

Example 9

On day 21 of the poultry farm trial of Example 8, a sample of poultry litter was taken and the litter was analysed by plating on agar plates. The plates were incubated and then stained by Gram staining. Only Gram positive species were present.

Example 10: Control of *Salmonella* Pathogens

Chicken manure was sterilized by autoclaving at a minimum temperature of 121° C. for 35 minutes, to ensure that the samples included no competing bacteria. After sterilization, the chicken manure was inoculated with *Salmonella enterica* and allowed to incubate for 24 hours. After incubation the non-control samples of chicken manure were treated with a composition of Example 6 by spraying approximately 100 µL of composition on the chicken manure (25 g). Control samples included sterilized chicken manure and sterilized chicken manure inoculated with *Salmonella enterica* and incubated for 24 hours but these controls were not treated with the composition of Example 6.

The samples were analysed for bacterial growth, both *Salmonella enterica* and *Bacillus subtilis* on growth media (ATCC medium 3, nutrient agar). The analysis of the controls were performed after sterilization (time 0), after inoculation and incubation for 24 hours (time 0) and the analysis of the test samples was carried out at 3, 6, 24, 48 and 96 hours after application of the composition of Example 6.

A supplemental Triple Sugar Iron (TSI) test, was used to distinguish between the growth of *Bacillus* spp. and *Salmonella* spp. *Salmonella enterica* produces hydrogen sulphide resulting in a dark colour in this test whereas the *Bacillus* spp. does not.

The presence of *Salmonella enterica* was assessed over a period of four days. After the four day period the test samples were re-innoculated with *Salmonella enterica* and incubated for 24 hours. The samples were then evaluated for a further period of four days. The samples for re-inoculation had been initially inoculated with *Salmonella enterica* incubated for 24 hours, treated with the composition of Example 5, incubated for 4 days, then reinoculated with *Salmonella enterica* and incubated for 24 hours. A sample was then analysed at time zero (control) then at 3, 6, 24, 48 and 96 hours. The results are shown in Table 2.

TABLE 2

| Sample | Description | Time (hrs) | Results | Comments |
|---|---|---|---|---|
| Control 1 | Sterilized chicken manure | 0 | No growth | — |
| Control 2 | Sterilized chicken manure inoculated with *S. enterica* | 0 | Growth | Growth positive for *S. enterica* by TSI test |
| Sample 1 | Sterilized chicken manure inoculated with *S. enterica* and treated with composition of Example 5 | 3 | Growth | TSI test negative for *Salmonella* |
| | | 6 | Growth | TSI test negative for *Salmonella* |
| | | 24 | Growth | TSI test negative for *Salmonella* |
| | | 48 | Growth | TSI test negative for *Salmonella* |
| | | 96 | Growth | TSI test negative for *Salmonella* |
| Control 3 | Treated sample reinnoculated with *S. enterica* | 0 | Growth | TSI test negative for *Salmonella* |
| Sample 2 | Sample 1 re-inoculated with *S. enterica* | 3 | Growth | TSI test negative for *Salmonella* |
| | | 6 | Growth | TSI test negative for *Salmonella* |
| | | 24 | Growth | TSI test negative for *Salmonella* |
| | | 48 | Growth | TSI test negative for *Salmonella* |
| | | 96 | Growth | TSI test negative for *Salmonella* |

There was no growth of pathogenic *Salmonella enterica* observed in any of the test samples treated with the composition of Example 6 from 3 hours to 96 hours. Furthermore, no growth of *Salmonella enterica* in the re-innoculated samples over 3 hours to 96 hours.

This demonstrates that the composition comprising a microorganism of the genus *Bacillus* and biosurfactant is effective against *S. enterica* found in chicken manure. The treatment is effective within 3 hours and has a long-lasting effect.

Example 11: Pest Control 25 gallons (95 L) of the composition of Example 6 was added to 400 gallons (1514 L) of water and sprayed on 21,000 square feet of poultry litter. The litter was then windrowed. The litter was checked for darkling beetle larvae and any larvae found were collected and monitored. The darkling beetle larvae expired within 2 hours of exposure to the litter treatment. No live darkling beetle larvae were found in the treated litter 24 hours after treatment.

Example 12: Control of *Campylobacter jejuni* Pathogen

Chicken manure was sterilized by autoclaving at a minimum temperature of 121° C. for 35 minutes, to ensure the samples included no competing bacteria. After sterilization, the chicken manure was inoculated with *Campylobacter jejuni*. The non-control samples of chicken manure was treated with a composition of Example 6 by spraying approximately 100 µL of composition on the chicken manure (25 g). Controls included sterilized chicken manure and sterilized chicken manure inoculated with *Campylobacter jejuni* but neither sample was treated with a composition of Example 6. The samples were incubated at 42° C.

The samples were analysed for bacterial growth on *Campylobacter jejuni* media. The analysis of the controls were performed after sterilization (time 0), after inoculation and incubation for 24 hours (time 0) respectively, and the analysis of the test samples was carried out at 3, 6, 24, 48 and 96 hours after application of the composition of Example 6.

After the 96 hour test period, the test samples were reinoculated with *Campylobacter jejuni*. A sample (control 4) was assessed at time 0 to confirm viability of the bacteria. The reinoculated samples were then incubated for 96 hours and assessed again. The results are shown in Table 3.

TABLE 3

| Sample | Description | Times (hrs) | Results |
|---|---|---|---|
| Control 1 | Sterilized chicken manure | 0 | No growth |
| Control 2 | Sterilized chicken manure inoculated with *C. jejuni* | 0 | Growth |

TABLE 3-continued

| Sample | Description | Times (hrs) | Results |
|---|---|---|---|
| Control 3 | Sample of Example 5 | 0 | No growth |
| Sample 1 | Sterilized chicken manure inoculated with C. jejuni and treated with composition of Example 5 | 3 | No Growth |
| | | 6 | No Growth |
| | | 24 | No Growth |
| | | 48 | No Growth |
| | | 96 | No Growth |
| Control 4 | Treated chicken manure reinoculated with C. jejuni | 0 | Growth |
| Sample 2 | Treated chicken manure with C. jejuni | 96 | No Growth |

There was no pathogenic *Campylobacter jejuni* observed in any of the test samples treated with a composition of Example 6 from 3 hours to 96 hours. Furthermore, no growth was observed in the reinoculated sample after 96 hours incubation.

This demonstrates that the composition comprising a microorganism of the genus *Bacillus* and biosurfactant is effective against *C. jejuni* found in chicken manure. The treatment was effective within 3 hours and has a long-lasting effect.

Example 13: Control of Ammonia in Poultry Egg Laying Facility

A four storey egg laying facility having birds in cages and manure falling onto conveyor belts was assessed for ammonia concentration. In the facility the manure from the top storeys is delivered by conveyor belt to a v-shaped platform door separating top and bottom floors. When the door opens, the manure (16000 lbs) is deposited onto a windrow approximately 6 feet high.

The windrow of manure was misted with a composition of Example 5 at 4 locations.

At locations 1 and 2, the composition was applied neat. At locations 3 and 4 the composition of Example 5 was applied diluted 1:16 with water. No fans were used if the ammonia levels remained below 50 ppm.

When the manure was left untreated and fans were not used to disperse the ammonia produced, ammonia levels in the facility reached 500 ppm. When fans were used, ammonia levels were reduced to <50 ppm.

The ammonia levels were sampled at intervals after treatment and the results are shown in Table 4.

TABLE 4

| Date | Time | Location 1 | Location 2 | Location 3 | Location 4 | Location 5 |
|---|---|---|---|---|---|---|
| 30/10 | 9.21 am | 19 ppm | 18 ppm | 23 ppm | 23 ppm | 25 ppm |
| 4/11 | 8.03 am | 46 ppm | 44 ppm | 50 ppm* | 52 ppm* | 56 ppm* |
| 10/11 | 3.10 pm | 30 ppm | 21 ppm | 30 ppm | 31 ppm | 41 ppm |
| 12/11 | 9.36 am | 11 ppm | 6 ppm | 13 ppm | 11 ppm | 19 ppm |
| 15/11 | 10.05 am | 26 ppm | 22 ppm | 42 ppm | 40 ppm | 40 ppm |
| 20/11 | 3.30 pm | 29 ppm | 24 ppm | 36 ppm | 41 ppm | 45 ppm |
| 22/11 | 8.29 am | 39 ppm | 28 ppm | 35 ppm | 36 ppm | 41 ppm |
| 24/11 | 9.40 am | 31 ppm | 29 ppm | 36 ppm | 40 ppm | 44 ppm |
| 28/11 | 7.51 am | 29 ppm | 39 ppm | 47 ppm | 53 ppm | 55 ppm |

*ineffective spraying resulted in increased ammonia levels but dropped upon reapplication correctly.

The results show that application of the composition of the invention to poultry manure was able to maintain ammonia levels below 50 ppm for more than 28 days.

In a variation, the manure may be treated by misting with a continuous low dosage while being deposited on the platform door or while located on the platform door to provide contact with more surface area.

Example 14: Alternative Biosurfactant Production

TABLE 5

| | Amount/ 150 L | Amount/ 1000 L |
|---|---|---|
| $KH_2PO_4$ 15 mM Monopotassium Phosphate (MW 136.09) | 306 gm | 2.04 Kg |
| $Na_2HPO_4$ 27.3 mM Disodium Phosphate (MW 141.96) | 581.25 gm | 3.87 Kg |
| $MgSO_4 \cdot 7H_2O$ 2.4 mM Magnesium Sulfate Heptahydrate (MW 246.48) | 88.7 gm | 592 gm |
| $CaCl_2 \cdot 6H_2O$ 7 µM Calcium Chloride Hexahydrate (MW 219.08) | 0.23 gm | 1.5 gm |
| $C_{10}H_{14}N_2Na_2O_8 \cdot 2H_2O$ 4 µM Disodium EDTA Dihydrate (MW 372.24) | 0.22 gm | 1.5 gm |
| $FeSO_4 \cdot 7H_2O$ 8 µM Ferrous Sulfate Heptahydrate (MW 284.05) | 0.34 gm | 2.3 gm |
| $MnSO_4 \cdot H_2O$ 10 mM Manganese Sulfate•Monohydrate (MW 151.0) | 226 gm | 1.51 Kg |
| $C_6H_{12}O_6 \cdot H2O$ 44 gm/L Glucose Monohydrate | 6.6 Kg | 44 Kg |
| Yeast extract 1% w/v | 150 gm | 1 Kg |
| $NH_4Cl$ 50 mM Ammonium Chloride (MW 53.49) | 400 gm | 2.67 Kg |
| $NaNO_3$ 50 mM Sodium Nitrate (MW 84.99) | 638 gm | 4.25 Kg |

An appropriate amount of filtered water was added to the bioreactor and bought to 35° C. The water was aerated continuously from this point. The nutrients listed above in Table 5 were added in the order given. Addition of ammonium and nitrate sources were added just before inoculation of the preparation to prevent any contaminating bacteria from growing because of lack of nitrogen. The innoculum was added in an amount to achieve an initial $OD_{66\ nm}$ of ≈0.15. The culture conditions and process were monitored by optical density measurements at $OD_{66\ nm}$.

Biosurfactant production was monitored by surface tension measurements. The surface tension of the broth can be titrated by measuring the culture fluid neat and making dilutions to determine the level of biosurfactant is above the Critical Micelle Concentration (CMC). The surface tension will not increase until the surfactin is diluted below the CMC.

The strain of microorganism may be monitored by culturing samples on MMS-Y and Blood Agar plates. If a mixed culture is used and the colony types can be differentiated on an agar plate, the inoculums and the final culture should be serially diluted to perform plate counts of each strain. This can not only determine the purity of the culture but also if one strain out competes the others.

Example 15: The Effect of Sulfate at Different Concentrations on Culture

The effect of sulfate on culture broth was tested by removing all sources of sulfate from the media and replacing them with chloride salts. The culture broth contained monopotassium phosphate/dipotassium phosphate buffer adjusted to pH 7 with potassium hydroxide. Samples were then spiked with varying concentrations of sodium sulfate (1.8 M) at 1 mL/L, 0.8 mL/L, 0.6 mL/L, 0.4 mL/L and 0.2 mL/L. Every half hour the optical density, pH and surface tension was evaluated. This test was done with the RSA-203 bacterial strain.

The results are shown in FIG. 1. The results show that the microorganisms grow equally well with chloride salts as they do with sulfate salts. In all samples, the surface tension had dropped and stabilized around 27 dynes by 5 hours.

This claims defining the invention are as follows:

1. A method for preparing a composition comprising endospores of *Bacillus subtilis* and at least one biosurfactant, the method comprising:
    a) culturing *Bacillus subtilis* RSA-203 (ATCC Accession No. PTA-13451) in a culture broth so as to encourage formation of a foamate enriched with the at least one biosurfactant;
    b) collecting and condensing the foamate from the culture broth to form a collected and condensed foamate;
    c) causing a culture comprising *Bacillus subtilis* to undergo endospore formation to produce a culture broth comprising the endospores of *Bacillus subtilis*; and
    d) combining the culture broth comprising the endospores with
        (i) an amount of the collected and condensed foamate comprising the at least one biosurfactant; and
        (ii) at least one anionic, cationic, non-ionic or zwitterionic surfactant, other than the at least one biosurfactant present in the foamate;
    thereby forming the composition;
    wherein the at least one biosurfactant in the composition is present in an amount of 2 mg/L to 7000 mg/L; and
    wherein the amount of the at least one biosurfactant in the composition is higher than in the culture broth comprising endospores.

2. The method according to claim 1, wherein the *Bacillus subtilis* in the composition is present in an amount of $1 \times 10^4$ cfu/mL to $1 \times 10^{13}$ cfu/mL.

3. The method according to claim 1, wherein the at least one biosurfactant is selected from surfactin, lichenysin, fengycin, iturin and mixtures thereof.

4. The method according to claim 3, wherein the at least one biosurfactant is selected from surfactin, lichenysin and mixtures thereof.

5. The method according to claim 4, wherein the at least one biosurfactant is surfactin.

6. The method according to claim 1, wherein the at least one biosurfactant is present in an amount of 50 to 7000 mg/L.

7. The method according to claim 1, wherein the surfactant has a hydrophilic lipophilic balance of 12 or greater.

8. The method according to claim 1, wherein the surfactant is an alkylbenzene sulfonic acid surfactant.

9. The method of claim 7, wherein the surfactant has a hydrophilic lipophilic balance of 12 to 14.

10. The method of claim 1, wherein the endospores of *Bacillus subtilis* comprise endospores of a microorganism other than *Bacillus subtilis* RSA-203.

* * * * *